United States Patent [19]

Tarter

[11] Patent Number: 5,465,833
[45] Date of Patent: Nov. 14, 1995

[54] DENTAL IMPRESSION MATERIAL PACKAGE

[76] Inventor: Norman D. Tarter, 70 41st St., Hickory, N.C. 28601

[21] Appl. No.: 41,828

[22] Filed: Apr. 1, 1993

[51] Int. Cl.⁶ .......................... A61B 19/02; B65D 25/08; B65D 30/24; F16K 51/00
[52] U.S. Cl. ...................... 206/63.5; 206/219; 251/149.3; 383/44; 383/904; 383/906
[58] Field of Search .................................. 206/63.5, 219, 206/221, 572; 433/214; 222/107, 556; 383/904, 906, 44, 43, 63; 604/407, 408, 415, 416; 251/149.7, 149.3, 149.2

[56] References Cited

U.S. PATENT DOCUMENTS

| | | | |
|---|---|---|---|
| 568,669 | 9/1896 | Ellsworth | 251/149.3 |
| 1,241,352 | 9/1917 | Doering et al. | 251/149.7 X |
| 2,317,545 | 4/1943 | Madsen et al. | 251/149.3 |
| 3,064,802 | 11/1962 | Jess et al. | 206/219 |
| 3,367,485 | 2/1968 | Schneider et al. | 383/44 X |
| 3,419,258 | 12/1968 | Ritchie | 206/219 |
| 3,430,842 | 3/1969 | Yamaguchi | 383/44 X |
| 4,023,675 | 5/1977 | Claasen . | |
| 4,362,198 | 12/1982 | Kemp | 383/63 |
| 4,670,053 | 6/1987 | Kooke et al. . | |
| 4,689,079 | 8/1987 | Buma et al. . | |
| 5,037,623 | 8/1991 | Schneider et al. . | |
| 5,052,554 | 10/1991 | Leonard . | |
| 5,116,222 | 5/1992 | Futami et al. . | |
| 5,259,844 | 11/1993 | Bilstad et al. | 604/408 |

*Primary Examiner*—Bryon P. Gehman
*Attorney, Agent, or Firm*—Rhodes, Coats & Bennett

[57] ABSTRACT

A dental impression powder package and method for the preparation of material for making dental impressions. The package includes a bag that encloses dental impression powder and a valve that extends through the bag. The valve is selectively adjustable between an open state where the water is injectable into the bag and a closed state in which fluids are prevented from passing through the valve. The valve includes an open top end, a closed bottom end, a wall extending between the top and bosom ends, and a slit extending along a section of the wall. When the valve is open, the slit opens to permit fluid to be inserted into the bag. The slit closes to block fluid from passing through the slit in the valve while the contents of the bag are being mixed. A syringe is insertable into the valve to insert water into the bag and to extract air from the bag. In one embodiment of the present invention, the alginate mixture is extruded from the bag through the valve and into an impression tray.

4 Claims, 2 Drawing Sheets

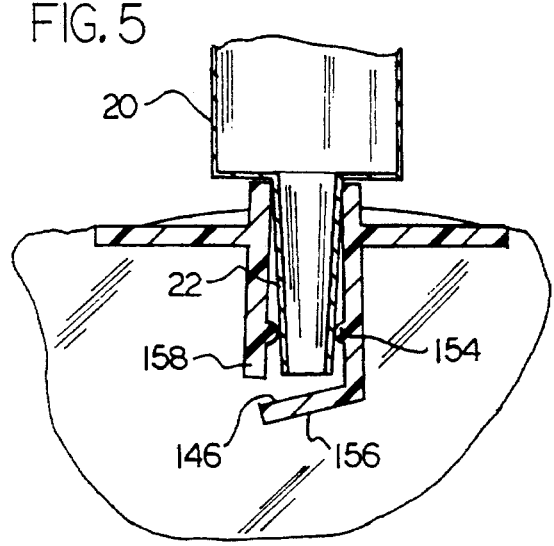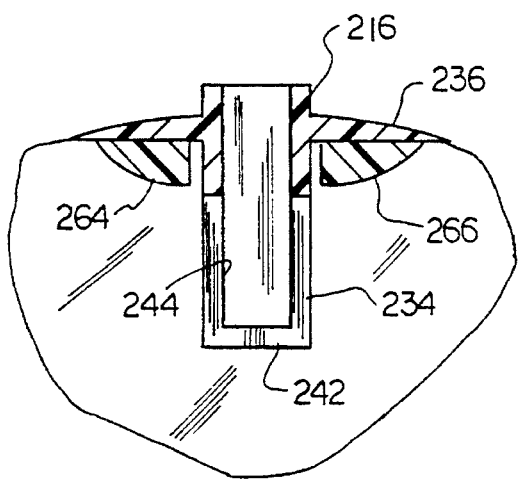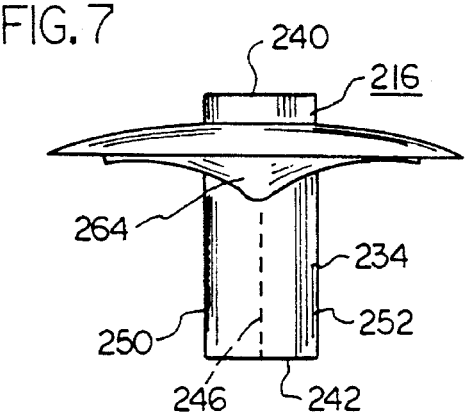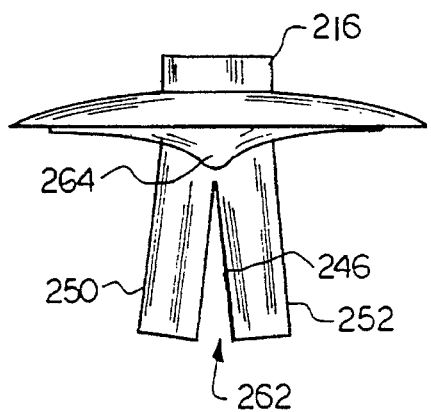

DENTAL IMPRESSION MATERIAL PACKAGE

FIELD OF THE INVENTION

This invention relates generally to dentistry, and more particularly to the preparation of material for making dental impressions.

BACKGROUND OF THE INVENTION

The typical dental office practice for preparing material for making dental impressions is to measure out alginate powder from a storage container with a measuring spoon into a mixing bowl, add water, and mix the water and alginate powder with a spatula. The alginate composition is then layered into the impression tray and used to make a dental impression. There are numerous problems with this prior art method of preparing the material used for making dental impressions. The most serious problem is the health risk resulting from a dentist, dental technician and/or the patient inhaling alginate powder during the handling of the alginate powder. When handling and mixing the powder, there is a release of powder into the air which may be inhaled by those nearby. Dentists and dental technicians run a serious risk of health problems caused by repeated inhalation of the alginate powder.

A second problem with the current typical dental office practice for making dental impressions is the difficulty of thoroughly mixing the alginate powder with water to produce a homogenous alginate mixture. When mixing water and the alginate powder with a spatula, the alginate mixture tends to entrain air within the mixture. These air bubbles and stratifications resulting from layering the composition into the impression tray decrease the quality of the impression that the alginate mixture is capable of producing. The strata can become separated in some cases, leading to poor impressions.

Another problem with the typical method of preparing material for making dental impressions is the excessive amount of time required for the complete process. The preparer must engage in numerous steps to prepare the alginate mixture. In addition, time must be taken to clean the spatula, mixing bowl, and any spilled powder after the preparation of the alginate mixture. But, because the alginate mixture tends to quickly set, the preparer is limited in the amount of time she can take mixing the alginate powder and water to help ensure thorough mixing.

U.S. Pat. No. 5,052,554, issued to Leonard, identifies certain problems with the current method of mixing together alginate powder and water in a mixing bowl. In the Leonard patent, a dental impression material package is disclosed for mixing alginate powder and water so as to eliminate the need for hand mixing alginate powder and water in a bowl. The dental impression material package of Leonard is filled with a measured amount of dental impression powder, and a frangible portion of the sealed bag is pierced by the nozzle of a syringe bulb to introduce water into the bag. The bag is then gripped at the pierced opening in the bag so that the powder in the bag can then be kneaded to mix the enclosed powder and water. When mixing is complete, a corner of the bag is cut and the mixed impression material is squeezed into the impression tray.

There are several problems with the dental impression material package of Leonard. The piercing of the bag by the syringe bulb leaves an opening in the bag that must be manually closed to prevent the contents of the bag from escaping. The need to manually close the opening in the bag makes it difficult to knead the bag, and more time may be required to fully mix the contents of the bag. Any additional time required to fully mix the powder and water within the bag will shorten the time available to the dental assistant to make the impression. In addition, because the alginate mixture begins to set so quickly, any increased time required to fully mix the contents of the bag may cause the alginate mixture to begin to set prior to the dental impression being taken.

Another problem with the dental impression material package and method of Leonard is the failure to teach a device or method for withdrawing air from the bag. Although Leonard acknowledges that air is undesirable and teaches to keep air out of the bag to the extent possible, air is still present. In particular, the addition of the water to the powder releases air from powder interstices. This excess air in the bag can result in of air becoming entrained in the alginate mixture during the mixing process so bubbles are still present.

SUMMARY OF THE INVENTION

The present invention is an improved dental impression material package and method that solves the problems discussed above. The dental impression package includes a bag or other flexible enclosure that encloses dental impression powder and a valve that extends through the bag. The valve allows selective insertion of water into the bag and also prevents the contents of the bag from inadvertently escaping when the powder and water are mixed within the bag. The valve is selectively adjustable between an open state where the water is injectable into the bag and a closed state where the contents of the bag are prevented from passing through the valve.

Structurally, the valve tube may include an open top end, a closed bottom end, and a circumferential wall extending between the top and bottom ends, and a slit extending along a section of the valve tube. When the valve is in the open state an opening is formed at the location of the slit so as to permit fluid to be inserted into the bag. The slit opening is closed when the valve is in the closed state so as to block fluid from passing through the slit in the valve while the contents of the bag are being mixed.

The invention may also include a syringe to permit a measured amount of water to be inserted into the bag through the valve. Preferably, insertion of a tip of the syringe into the valve opens the valve. After the water is inserted the syringe may be used to withdraw any air in the bag including air liberated from the alginate powder by the water.

Since the alginate powder is always contained in the bag as long as it is in powder form, no dust is released that can be inhaled. Also the dust does not scatter, so general dental office cleaning is less burdensome. And, the quality of the dental impressions is improved because the alginate paste contains fewer bubbles and is not stratified when deposited in the impression tray. The time and subsequent clean-up required to prepare the mixture is reduced, lowering personnel costs, a matter of much concern in these days of escalating health care costs.

Moreover, the invention is more readily transportable, consisting of self-contained, pre-measured bags, with a portable syringe. This adapts itself well to field work and travel situations.

BRIEF DESCRIPTION OF THE DRAWINGS

FIG. 5 is a cross-sectional view of the second embodiment of the valve employed in the present invention, showing the valve in an open state;

FIG. 6 is a cross-sectional view of a third embodiment of the valve employed in the present invention showing the valve in the closed state;

FIG. 7 is a rotated, side view of the third embodiment of the valve employed in the present invention, showing the valve in the closed state; and FIG. 8 is a side view of the third embodiment of the valve employed in the present invention, showing the valve in the open state.

DETAILED DESCRIPTION OF THE PREFERRED EMBODIMENT

Figure 1:
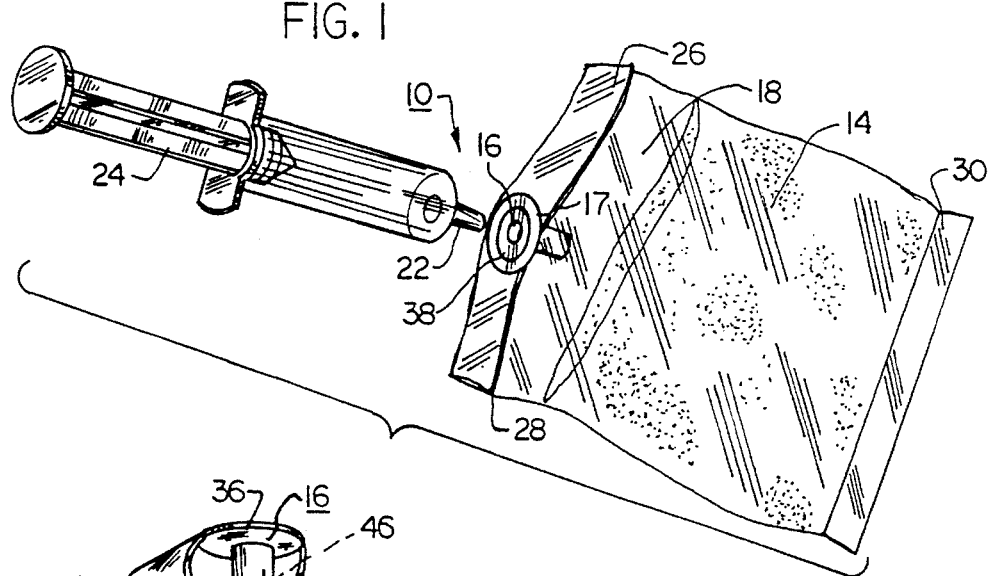
FIG. 1 is a perspective view of an embodiment of the dental impression material package of the present invention.

Referring to the drawings, the dental impression material package of the present invention is indicated generally by the numeral 10. Material package 10 is used to mix alginate powder and water to produce an alginate mixture for making dental impression molds. Structurally, package 10 includes an enclosure such as a bag 12 that encloses an alginate powder 14 and a valve 16 for allowing the selective introduction of water into an enclosed space 18 of bag 12. A syringe having a tapered nozzle 22 and plunger 24, or other water delivery device, is used to inject water through valve 16. Preferably, the syringe has graduation markings to permit a measured amount of water to be taken up by the syringe for injections into the bag. The water amount will be coordinated with the powder amount in conventional fashion. Powder 14 and water injected into the bag 12 can then be mixed together to form an alginate mixture.

Bag 12 is made from a transparent plastic material and has an enclosed top 26 and a bottom portion 30. Top portion 26 of bag 12 includes valve 16 connected by an encircling heat-seal line 38. A protective bag flap 28 covers valve 16 and is also secured at heat-seal line 38. Bag flap 28 covers valve 16 and prevents impurities from entering the valve 16 prior to use. Also, the flap 28 permits the bag to be vacuum sealed at the time of manufacture to reduce the volume of the bag t be shipped this makes the bag firm, providing assurance t the user that the bag has not been punctured if it is firm the vacuum sealing also insures a longer shelf life. Various other ways to seal the valve may be substituted. The seal may be omitted entirely, but that is not preferred.

Valve 16 has an integrally-formed peripheral flange 17 to which the bag 12 is sealed at line 38. Bottom portion 30 may include an openable/closeable seal 32 that enables a user to selectively deposit a selected amount of alginate powder into enclosed space 18 and then to reseal bag 12. The openable/closeable seal 32 may be a ZIPLOC® type seal. However, in a preferred embodiment, bag 12 is filled with alginate powder and heat sealed along bottom portion 30.

Also, the valve can be provided located totally within the bag, heat sealed, so that the wall of the bag covers the opening in the valve to seal it shut. Then, puncturing the wall at a point aligned with the opening will allow valve-controlled access to the interior of the bag.

Figure 2:
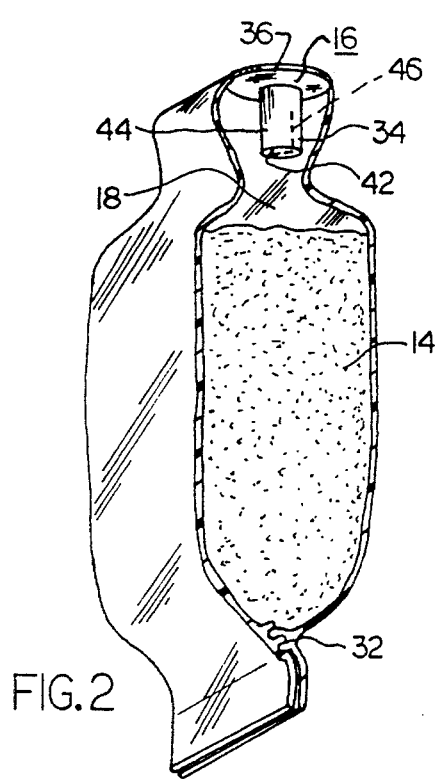
FIG. 2 is a cross-sectional view of a first embodiment of the valve employed in the present invention showing the valve in a closed state.
Figure 3:
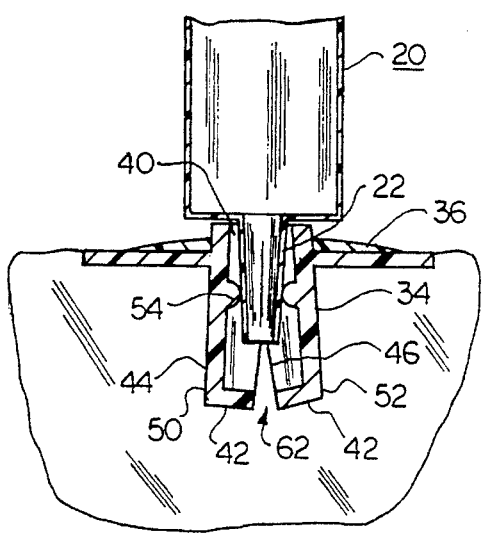
FIG. 3 is a cross-sectional view of the first embodiment of the valve employed in the present invention, showing the valve in an open state.

Package 10 may be provided with any of several embodiments of valve 16 to allow introduction of water into enclosed space 18 of bag 12. FIGS. 2–3 illustrate a first embodiment of valve 16. Valve 16 of the first embodiment includes a tube 34 and a disk 36, both made from a rigid, but deformable plastic. The disk 36 encircles and projects outwardly from tube 34 and is used as a mount to secure valve 16 to bag 12.

Tube 34 extends through a center section of disk 36 to form a fluid passageway. Tube 34 includes an open top 40, a substantially closed bottom 42, and a cylindrical wall 44 extending between top 40 and bottom 42 of tube 34. As shown in FIG. 2 and 3, slits 46 extends vertically downward along opposing sections of wall 44 and across closed bottom 42 to form a first lower half section 50 and a second lower half section 52 of tube 34. A ring 54 is attached to wall 44 and projects inwardly toward a center axis of valve tube 34. Interior ring 54 is located just above first and second lower half sections 50 and 52.

As shown in FIG. 2, valve 16 is biased in a closed state where tube 34 is in a non-flow position and acts as a barrier to fluid passing to or from the enclosed space 18 of bag 12. In particular, first and second lower half sections 50 and 52 of valve tube 34 are biased together at the location of slit 46 such that water or other fluid cannot freely pass through tube 34. Valve 16 moves from the biased closed state shown in FIG. 2 to the open state shown in FIG. 3 by inserting the tapered nozzle 22 of syringe 20 into tube 34. As nozzle 22 is inserted through top opening 40 of tube 34, interior ring 54 engages nozzle 22 and wall 44 is forced outwardly. First and second lower half sections 50 and 52 separate at slit 46 to form a slit opening 62, putting valve 34 in an open state. Fluid from syringe 20 can then dispensed through slit opening 62. The force of the water passing through nozzle 22 also creates water pressure within tube 34 that tends to spread first lower and second lower half sections 50 and 52 apart. The removal of nozzle 22 from tube 34 removes the outward force against wall 44 to cause first and second lower half sections 50 and 52 to move inwardly and close opening 62. When valve 16 is in the closed state, alginate powder 14 and water can be mixed by kneading bag 12, and valve 16 prevents the contents of bag 12 from escaping. The top of the bag desirably includes a flap 19 that over the top of the valve so as to provide a barrier to passage of impurities into the valve prior to use.

Figure 4:
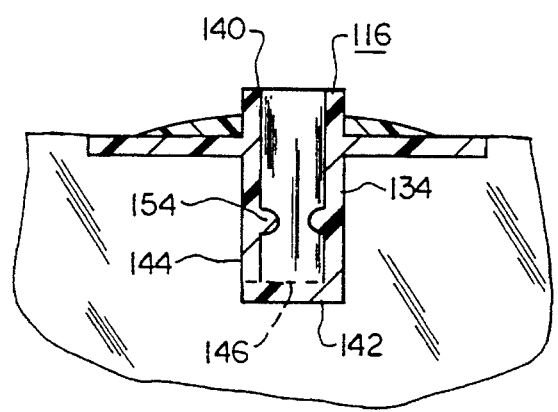
FIG. 4 is a cross-sectional view of a second embodiment of the valve employed in the present invention, showing the valve in a closed state.

FIGS. 4 and 5 show a second embodiment of valve 116. The second embodiment of valve 116 is identical to the first embodiment shown in FIGS. 2–3 with the exception of the location of slit 146 on tube 134. In the second embodiment of valve 116, slit 146 partially encircles the cylindrical tube 134 and is positioned on wall 144 towards closed bottom 142. Slit 146 divides tube 134 into a lower section 156 and an upper section 158. As shown in FIG. 4, valve 116 of the second embodiment is biased in a closed state so that tube 134 provides a barrier to fluids. To open valve 116 of the second embodiment, nozzle 22 of syringe 20 is inserted into tube 134. Nozzle 22 engages interior ring 154 and forces wall 144 outwardly to help force lower section 156 and upper section 158 to spread at the location of slit 146. The ring 154 (as well as the rings of other embodiments) also helps hold the nozzle of the syringe in place in the valve. The lower section 156 of tube 134 is also forced downwardly by water pressure from water forced downwardly syringe 20. Removal of nozzle 22 from tube 134 and removal of water pressure within tube 134 causes tube 134 to return to its normally biased closed state.

FIGS. 6–8 show a third embodiment of the valve 216. Valve 216 of the third embodiment also includes a tube 234 with a disk 236 extending outwardly from the tube 234. Tube 234 includes a top opening 240, a closed bottom 242, and a peripheral wall 244 extending between the top and bottom 240 and 242.

As shown in FIGS. 6–8, the third embodiment of valve 216 includes a pair of flanges 264 and 266 attached to and extending downwardly from a lower surface of disk 236. Flanges 264 and 266 are positioned adjacent to opposite side sections of wall 244 and extend downwardly just above slit 246.

As shown in FIGS. 6 and 7, valve 216 is typically in a closed state where first and second half sections 250 and 252 are disposed adjacent one another, and valve tube 234 is in the non-flow position. To open valve 216, disk 236 is pinched downwardly so that flanges 264 and 266 are forced against opposite sides of wall 244. Pressing flanges 264 and 266 inwardly against wall 244 forces first and second lower half sections 250 and 252 apart at slit 246 such that slit opening 262 is formed. Flanges 264 and 266 enable a user to selectively position the valve 216 between the open and closed states independent of the insertion of syringe 20 in valve 216. If desired, the valve can be made with inwardly tapering walls or a ring like ring 54, so that insertion of the nozzle of the syringe opens the valve.

In operation, the dental impression material package 10 of the present invention is used by a dental assistant, dental technician or dentist to prepare material for making dental impressions in the following manner. First, if the bag is of the ZIPLOC® type, the quantity of powder 14 to be mixed is determined by opening the openable/closeable seal 32 of bag 12 and depositing a selected quantity of powder 14 into the bag. The openable/closeable seal 32 is then closed to seal powder 14 within bag 12. The step of depositing a selected quantity of powder in the bag is eliminated if a heat sealed, pre-filled bag 12 is used, as is preferable. A selected amount of water is drawn into syringe 20 for mixing with powder 14 in bag 12. The water within syringe 20 can then be inserted into bag 12 for mixing with powder 14. Water from nozzle 22 flows out of opening 62, 162, 262 and is sprayed outwardly from opposite sides of wall 44, 144, 244 and from bottom 42, 142, 242 such that the water sprays from tube 34, 134, 234 in an arc. The spraying of water into bag 12 in a plurality of directions helps mix the water and alginate powder so as to speed the mixing process. After all the water from syringe 20 has been injected into bag 12, syringe plunger 24 is pulled back to remove air from bag 12.

The precise method of inserting water into bag 12 and other steps in the method of preparing the alginate mixture vary according to which embodiment of the valve 16 is attached to bag 12. The use of packages 10 where the first and second embodiments of valve 16 are used will be described separately from the use of packages 10 having the third embodiment of valve 16.

Referring to FIGS. 2–3, to inject water into enclosed space 18, nozzle 22 of syringe 20 is forced through the protected bag flap 28 which covers top 40 of tube 34. Nozzle 22 is then forced downwardly into tube 34 where nozzle 22 engages interior ring 54 and forces tube wall 44 outwardly. First and second lower half sections 50 and 52 are forced apart by nozzle 22 such that opening 62 is formed. Water is then injected from syringe 20 into the enclosed space 18 of bag 12.

After water contained within syringe 20 has been inserted into bag 12, the water and powder are lightly kneaded, liberating air from the powder. The plunger 24 of syringe 20 is pulled outwardly to withdraw the air contained within enclosed space 18 of bag 12. Removal of air from enclosed bag 12 helps to prevent air bubbles from being formed in the alginate mixture.

Syringe 20 is then removed from valve 16, causing valve 16 to close. Because valve 16 is constructed from a flexible material, first and second lower halves 50 and 52 spring together to close opening 62 as nozzle 22 is removed. The dentist or technician then kneads bag 12 to mix the enclosed powder and liquid within bag 12 and produce the alginate mixture. While bag 12 is being kneaded, valve 16 remains closed and prevents the powder 14 and liquid (and paste-like composition) within the bag from escaping. Because valve 16 automatically closes upon removal of syringe 20 and remains closed until reinsertion of syringe 20, the dentist or technician is then able to use both hands to knead bag 12 and more quickly mix the enclosed powder and liquid together.

After thoroughly mixing the contents of bag 12, the dentist opens the openable/closeable seal 32 and squeezes bag 12 to extract the alginate mixture through seal 32 and into an impression tray. If the bag 12 is heat sealed along bag bottom 30, the dentist uses scissors or another implement to cut open bag 12 and squeeze the alginate material into the impression tray. Openable/closeable seal 32 eliminates the need for scissors. After extraction of the alginate mixture from bag 12, bag 12 and attached valve 16 can be disposed. The embodiment FIGS. 4–5 is used similarly, but the water's spray pattern is more lateral than in the first embodiment.

A dental impression package 10 employing the third embodiment of valve 216 operates as follows. Nozzle 22 of syringe 20 is forced through protective bag flap 28 (not shown) and into tube 234. Insertion of nozzle 22 into valve tube 234 does not cause valve 216 open. To open valve 216, the dentist or technician presses downwardly against disk 236 at a location above flanges 264 and 266. Flanges 264 and 266 are forced against opposite sections of wall 244 at a location adjacent slit 246. The pressing of flanges 264 and 266 against wall 244 deforms tube 234, forcing first and second lower half sections 250 and 252 apart such that opening 262 is formed. The dentist or technician then injects water from the syringe through top opening 240 of tube 234.

Valve 216 is closed by releasing the downward force exerted against disk 236 to allow disk 236 to return to its original, generally horizontal position. As disk 236 moves to its initial position shown in FIGS. 6 and 7, flanges 264 and 266 disengage valve wall 244, and first and second lower half sections 250 and 252 move together to close opening 262. Bag 12 is then kneaded to thoroughly mix the powder 14 and water contained therein. The contents of bag 12 do not escape during the kneading of the bag 12 because valve 216 is closed, so fluid is prevented from passing through the valve 216.

To release the alginate mixture from bag 12, the dentist opens valve 216 by again pinching the disk 234 and squeezes the bag 12 to cause the alginate mixture to be extruded through valve 216 and into the impression tray. The ability to extrude the alginate mixture through the valve 216 eliminates the need of clipping an opening in the bag 12. Furthermore, by extruding the mixed impression material through the valve, the valve acts like a small homogenizer helping to further mix the alginate mixture. Used bag 12 and attached valve 216 can then be thrown away. Cleaning after the preparation of the material for making dental impressions is minimized.

The package 10 of the present invention provides for a more efficient and safer device and method for the preparation of material used to make dental impressionst. Airborne alginate powder is avoided to prevent inhalation of the alginate powder by the preparer of the material used for making dental impressions and others, including the patent. Also, the selectively openable and closeable valve 16, 116, 216 allows for more effective mixing of the alginate powder 14 with water. Since the material is extruded from the bag, the stratification which results from layering material into a tray with a spatula is avoided. In addition, the disposable nature of package 10 makes the overall process more efficient.

Conventional alginate composition batches are made up in varying sizes, depending on the size of the dental impression to be made. The present invention can be provided in the form of varying bags holding varying amounts of powder, with appropriate measured amounts of water being added. In the embodiment having a recloseable opening such as the ZIPLOC® opening, a measured amount of powder may be introduced into the bag. The present invention may, of course, be carried out in other specific ways than those herein set forth without departing from the spirit and essential characteristics of the invention. For example, instead of using a dedicated syringe, a dentist may use a suitable water spray device, typically readily available as installed in dental consoles. The amount of water may be estimated by the bag being made in such a size that when the water becomes turgid, a proper amount of water is present. In such a case the valve 216 is preferred since it permits release of air from the bag.

Also the dry mixture in the bag may be a multi-part mixture, such as with the dental stone. Or, the bag can contain a liquid to which a second liquid is to be added. The present embodiments are, therefore, to be considered in all respects as illustrative and not restrictive and all changes coming within the meaning and equivalency range of the appended claims are intended to be embraced therein.

What is claimed is:

1. A dental impression powder package comprising:
   (a) a bag enclosing dental impression powder; and
   (b) a valve extending through said bag including a valve tube having a top end, a bottom end, a wall extending between the top and bottom ends, and a slit extending along a section of the wall and openable to open said valve, said valve being adjustable between an open state and a closed state and including a first flange disposed adjacent the valve tube, the first flange positionable against the valve tube to selectively open the valve tube, wherein fluid is selectively insertable into the bag through the valve when the valve is in the open state by pressing the first flange against the valve tube and injecting fluid from a water delivery device into the bag, fluid is blocked from flowing through the valve when the valve is in the closed state so that a fluid can be selectively introduced into the bag for mixture with said powder to produce a mixed impression material and mixed impression material within the bag is extractable from the bag through the valve tube by pressing the first flange against the valve tube and squeezing the bag.

2. The dental impression powder package of claim 1 wherein the first flange is disposed adjacent to the slit.

3. The dental impression powder package of claim 1 wherein the valve includes a second flange disposed on an opposite side of the wall relative to the first flange, and wherein the first and second flanges are positionable against the valve tube to selectively open the valve.

4. The dental impression powder package of claim 3 wherein the valve includes a disk extending outwardly from the valve tube, the disk being flexible and having the first and second flanges attached thereto, wherein the disk is moveable to selectively position the first and second flanges against the valve tube to open the valve.

\* \* \* \* \*